(12) United States Patent
Fukuda et al.

(10) Patent No.: US 8,841,250 B2
(45) Date of Patent: Sep. 23, 2014

(54) METHOD FOR PROMOTING MUSCLE REPAIR COMPRISING ADMINISTERING G-CSF AT THE SITE OF INJURY

(71) Applicant: Keiichi Fukuda, Tokyo (JP)

(72) Inventors: Keiichi Fukuda, Tokyo (JP); Shinsuke Yuasa, Tokyo (JP); Mie Hara, Tokyo (JP)

(73) Assignee: Keiichi Fukuda, Tokyo (JP)

( * ) Notice: Subject to any disclaimer, the term of this patent is extended or adjusted under 35 U.S.C. 154(b) by 0 days.

(21) Appl. No.: 13/942,270

(22) Filed: Jul. 15, 2013

(65) Prior Publication Data

US 2013/0302271 A1 Nov. 14, 2013

Related U.S. Application Data

(62) Division of application No. 13/319,570, filed as application No. PCT/JP2009/069672 on Nov. 16, 2009, now abandoned.

(30) Foreign Application Priority Data

May 14, 2009 (JP) ................. 2009/117795

(51) Int. Cl.
*A61P 17/02* (2006.01)
*A61K 38/19* (2006.01)
*C07K 14/535* (2006.01)

(52) U.S. Cl.
CPC ............ *A61K 38/193* (2013.01); *Y10S 930/145* (2013.01)
USPC ............ 514/9.4; 514/9.7; 514/21.2; 530/351; 530/395; 930/145

(58) Field of Classification Search
None
See application file for complete search history.

(56) References Cited

FOREIGN PATENT DOCUMENTS

| EP | 1 632 241 A1 | 3/2006 |
|---|---|---|
| JP | 2005-206544 A | 8/2005 |
| WO | WO 2005049062 A1 * | 6/2005 |

OTHER PUBLICATIONS

Stratos, et al., "Granulocyte-colony stimulating factor enhances muscle proliferation and strength following skeletal muscle injury in rats", J. Appl. Physiol., 2007, pp. 1857-1863, vol. 103, No. 5.
Naito, et al., "Administration of granulocyte colony-stimulating factor facilitates the regenerative process of injured mice skeletal muscle via the activation of Akt/GSK3aβ signals", Eur. J. Appl. Physiol., Mar. 2009, pp. 643-651, vol. 105, No. 4.
Paoni, et al., "Time course of skeletal muscle repair and gene expression following acute hind limb ischemia in mice", Physiol Genomics, 2002, pp. 263-272, vol. 11, No. 3.
Extended European Search Report dated Oct. 15, 2012, issued in Application No. 09844652.9 (six pages).

* cited by examiner

*Primary Examiner* — Zachary Howard
(74) *Attorney, Agent, or Firm* — Browdy and Neimark, PLLC (57) ABSTRACT

The present invention relates to muscle repair promoters for local application that contain a colony-stimulating factor (CSF) as an active ingredient. The muscle repair promoters of the present invention exhibit their effect at low doses, particularly when they are administered intramuscularly.

15 Claims, 6 Drawing Sheets

METHOD FOR PROMOTING MUSCLE REPAIR COMPRISING ADMINISTERING G-CSF AT THE SITE OF INJURY

RELATED APPLICATIONS

This is a divisional of application Ser. No. 13/319,570, filed Jan. 25, 2012, which is the U.S. National Phase application of International Application No. PCT/JP2009/069672, filed Nov. 16, 2009, such application claiming the benefit of Application No. 117795/2009 filed in Japan on May 14, 2009, the entire contents of each of which are incorporated herein by reference.

TECHNICAL FIELD

The present invention relates to muscle repair promoters. The muscle repair promoters of the present invention contain a granulocyte colony stimulating factor (G-CSF) as an active ingredient.

BACKGROUND ART

Adult skeletal muscle has its own stem cells, called satellite cells which are responsible for generating new muscle in pathological and physiological condition. These muscles have regeneration potency but their power is not infinite (Non-patent Document 1). There are many incurable skeletal muscle diseases like skeletal muscle dystrophy, myopathy, severe injury, and disuse syndrome (Non-patent Document 2). So it should be extremely useful to elucidate the mechanism of skeletal muscle regeneration and develop a novel regeneration therapy using it. Skeletal muscle development and regeneration are precisely regulated by many various growth factors and cytokines but the regeneration of skeletal muscle cells is not well controllable (Non-patent Document 3). The present inventors previously screened humoral factors and receptors during the cardiomyocyte differentiation of embryonic stem (ES) cells (Non-patent Document 4).

The granulocyte colony stimulating factor (G-CSF) was initially identified as a hematopoietic cytokine and has been used for the mobilization of hematopoietic stem cells in clinics (Non-patent Documents 5, 6, and 7). In addition, G-CSF has various roles in cell differentiation, proliferation and survival (Non-patent document 8).

It was also reported that G-CSF had an action for proliferating muscle cells of rats undergoing skeletal muscle injury so as to enhance the muscle recovery (Non-patent Document 9). However, if G-CSF is involved in the regeneration of skeletal muscle, there are no reports about the underlying mechanism and about the appropriate method, frequency and dosage of actual administration of G-CSF as a muscle repair promoter.

The following is the prior art reference information relevant to the invention of the subject application.

CITATION LIST

Non-Patent Document

Non-patent Document 1: Le Grand, F. & Rudnicki, M. A. Skeletal muscle satellite cells and adult myogenesis. Current Opinion in Cell Biology 19, 628-633 (2007)

Non-patent Document 2: Shi, X. & Garry, D. J. Muscle stem cells in development, regeneration, and disease. Genes & Development 20, 1692-1708, doi:10.1101/gad.1419406 (2006)

Non-patent Document 3: Buckingham, M. & Montarras, D. Skeletal muscle stem cells. Current Opinion in Genetics & Development 18, 330-336 (2008)

Non-patent Document 4: Yuasa, S. et al. Transient inhibition of BMP signaling by Noggin induces cardiomyocyte differentiation of mouse embryonic stem cells. Nat Biotechnol 23, 607-611 (2005)

Non-patent Document 5: Welte, K., Gabrilove, J., Bronchud, M. H., Platzer, E. & Morstyn, G. Filgrastim (r-metHuG-CSF): the first 10 years. Blood 88, 1907-1929 (1996)

Non-patent Document 6: Demetri, G. D. & Griffin, J. D. Granulocyte colony-stimulating factor and its receptor. Blood 78, 2791-2808 (1991)

Non-patent Document 7: Metcalf, D. Hematopoietic cytokines. Blood 111, 485-491, doi:10.1182/blood-2007-03-079681 (2008)

Non-patent Document 8: Avalos, B. R. Molecular analysis of the granulocyte colony-stimulating factor receptor. Blood 88, 761-777 (1996)

Non-patent Document 9: Stratos, I. et al., Granulocyte-colony stimulating factor enhances muscle proliferation and strength following skeletal muscle injury in rats, J. of Applied Physiology, 103, 1857-1863 (2007)

SUMMARY OF INVENTION

Solution to the Problem

The present invention aims to provide muscle repair promoters which contain G-CSF as an active ingredient. It particularly aims to elucidate the effect G-CSF may exert on damaged muscle and the mechanism by which the effect is exerted, as well as determining the appropriate method, frequency and dosage of administration of G-CSF as a muscle repair promoter so as to provide practically feasible muscle repair promoters that contain G-CSF as an active ingredient.

Means for Solving the Problems

The present inventors studied the effect G-CSF might exert on damaged muscle and the mechanism by which the effect would be exerted. As a result, they found the following: a G-CSF receptor had been expressed in somites of mouse embryo and the proliferation of myoblasts was promoted when G-CSF was administered; the G-CSF receptor was strongly expressed at 4 to 7 days after skeletal muscle injury; when G-CSF was locally administered in that period, low doses were sufficient for the skeletal muscle to be promoted markedly. The present invention has been accomplished on the basis of these findings.

Thus, the present invention provides the following.

[1] A muscle repair promoter for local administration, which contains a granulocyte colony stimulating factor (G-CSF) as an active ingredient.

[2] The muscle repair promoter as recited in 1 above, wherein the local administration is intramuscular administration.

[3] The muscle repair promoter as recited in 1 or 2 above, which is to be administered at 2-10 days after muscle injury.

[4] The muscle repair promoter as recited in any one of 1 to 3 above, which is to be administered at an interval of 4 days.

[5] The muscle repair promoter as recited in 3 or 4 above, which is to be administered in a total dosage of 0.2-50 µg/kg within the period of 2-10 days after muscle injury.

Advantageous Effect of Invention

The muscle repair promoters of the present invention showed an extremely marked muscle repair promoting effect at low doses upon local administration, particularly upon intramuscular administration. The muscle repair promoters of the present invention are effective for the treatment of various types of muscle injury.

BRIEF DESCRIPTION OF DRAWINGS

FIG. 1 is a set of photographs showing that G-CSFR is expressed in the developing somites after mid-gestation;
a. Whole-mount in situ hybridization for c-met, pax3, myod, mrf4, and csf3r, as well as LacZ staining of myf5 knock-in E10.5 embryo; csf3r was expressed in the somite at E10.5.
b. Immunostaining for G-CSFR and DAPI in E8.5, E9.5, E10.5, and E11.5 mouse embryos (horizontal section); G-CSFR (green) was clearly expressed during E9.5 to E10.5 in the somite. c. Triple-immunofluorescent stainings for Pax3, Pax7 and G-CSFR at E10.5 embryo; G-CSFR (Green), Pax3, Pax7 (Red), and nuclei (DAPI, blue) are shown. d. Triple-immunofluorescent stainings for MyoD and Myogenin, Desmin, and G-CSFR at E10.5 embryo are shown. e. Triple-immunostainings for G-CSF (Green), Pax3, Pax7 (Red), and nuclei (DAPI, blue) are shown. f. Triple-immunofluorescent stainings for MyoD and Myogenin, Desmin, and G-CSF (green) at E10.5 embryo are shown. Note that both G-CSF and G-CSFR were expressed in the same cell.

FIG. 2 shows the increase in the proliferation of myoblast cells due to G-CSF;
a. Phase contrast photograph and immunofluorescent photograph for G-CSFR and α-actinin of C2C12 cells before and after differentiation. b. Western blot analysis of the C2C12 cells at various time pointes after differentiation; the α-actinin expression increased gradually while G-CSFR was progressively downregulated after differentiation. c. Effect of G-CSF on the proliferation of C2C12 cells; G-CSF was found to increase the number of C2C12 cells in a dose-dependent manner. d. Effect of G-CSF on the BrdU uptake in C2C12 cells. e, Effect of anti-G-CSF blocking antibody on the serum-induced proliferation of C2C12 cells; anti-G-CSF blocking antibodies inhibited serum-mediated proliferation in a dose-dependent manner. f. Western blot analysis of phosphorylation of the representative signaling molecules such as STAT3, AKT, ERK, JNK, and p38MAPK in C2C12 cells; G-CSF induced phosphorylation of STAT3, AKT, ERK, JNK, and p38MAPK in a time-dependent manner. g. G-CSF activated APRE luciferase activity in C2C12 cells in a dose-dependent manner.

FIG. 3 shows that G-CSF receptor is expressed in adult regenerating skeletal myocytes;
a. Cardiotoxin injury model and the timing of histological analysis. b. Histological analysis of the cardiotoxin-injured skeletal muscle; HE staining of rectus femoris; skeletal muscle injury and its regeneration process are clearly shown. c, d. Triple immunostainings of the non-injured (c, Day 0) and injured skeletal muscle (d, Day 5) for G-CSFR (Green), Laminin (Red), and nuclei (DAPI, blue) are shown; G-CSFR was not expressed at day 0, while small, round in shape and central nuclear regenerating myocytes strongly expressed G-CSFR at 5 days after injury. e, Time course of the expression of G-CSFR in the regenerating skeletal myocytes; immunofluorescent staining of the injured skeletal muscle at days 1, 5, 8 and 14 is shown. f. G-CSFR positive cells and centronuclear cells were counted; the percentage of G-CSFR positive cells over the centronuclear cells was counted; the G-CSFR positive regenerating skeletal muscle cells were observed at 3 to 8 days after the injury.

FIG. 4 shows that both intrinsic and extrinsic G-CSF augments skeletal muscle regeneration;
a. Effect of intravenous (i.v.) or intramuscular (i.m.) administration of G-CSF on cardiotoxin-induced skeletal muscle injury; HE stainings of injured rectus femoris at 7 days after cardiotoxin injection are shown; a number of central nuclear skeletal muscle cells fairly increased, and the regeneration was promoted by administration of extrinsic G-CSF; i.m. administration was more efficient than i.v. administration. b. The number of central nuclear cells was quantitated; G-CSF significantly increased the regenerated central nuclear skeletal myocytes. c. Diameter of the regenerated rectus femoris was measured; intramuscular administration of G-CSF was efficient for the regeneration. d. Measurement of hand grip strength after cardiotoxin injury; G-CSF significantly improved the muscle strength of the cardiotoxin-induced injured skeletal muscle. e. Role of intrinsic G-CSF signal on skeletal muscle regeneration; HE stainings of injured rectus femoris at day 7 are shown; administration of the anti G-CSF neutralizing antibody at day 3 deteriorates the spontaneous skeletal myocyte regeneration in a dose-dependent manner. f. The number of central nuclear cells was counted; the anti G-CSF neutralizing antibody significantly decreased the regenerated central nuclear skeletal myocytes. g. Diameter of the injured rectus femoris was also significantly decreased by the anti-G-CSF neutralizing antibody.

FIG. 5 shows impaired skeletal muscle development and regeneration in csf3r$^{-/-}$ mouse;
a. HE staining of rectus femoris from the wild type and csf3r$^{-/-}$ mice is shown; each myocyte section in csf3r$^{-/-}$ mice had a larger diameter than in the wild type. b. Quantitative analysis of the skeletal myocyte sectional area was made in the wild type and csf3r$^{-/-}$ mice. c. The diameter of rectus femoris is shown; csf3r$^{-/-}$ mice show a significant decrease in the size of the rectus femoris. d. HE staining of the cardiotoxin-induced injured skeletal muscle at day 7 and 14 in the wild type and csf3r$^{-/-}$ mice; the muscle regeneration process was markedly delayed in csf3r$^{-/-}$ mice. e. Measurement of the number of central nuclear myocytes in regenerating skeletal muscle at day 7 or 14 in the wild type and csf3r$^{-/-}$ mice; muscle regeneration was markedly hindered in csf3r$^{-/-}$ mice. f. Effect of extrinsic G-CSF administration on the cardiotoxin-induced muscle injury in the wild type and csf3r$^{-/-}$ mice; HE staining of the injured skeletal muscle at day 7 after cardiotoxin injection.
g. Effect of extrinsic G-CSF administration on cardiotoxin-induced skeletal myocyte injury, as measured by the number of central nuclear myocytes; accelerated muscle regeneration due to extrinsic G-CSF was not observed in csf3r$^{-/-}$ mice. h. Hand grip strength was also measured in cardiotoxin-injected csf3r$^{-/-}$ mice with or without G-CSF treatment; G-CSF did not improve the functional recovery in csf3r$^{-/-}$ mice.

FIG. 6 shows the role of G-CSFR expressing hematopoietic cells on skeletal muscle regeneration;
a. Experimental model using bone marrow transplantation 1; bone marrow was isolated from GFP-transgenic mice and transplanted into the csf3r$^{-/-}$ mice; cardiotoxin was injected into rectus femoris and G-CSF was administered at day 4 and 6. b. The chimerism of hematopoietic cells before (left) and after (right) bone marrow cell transplantation were analyzed by FACS. c, d. Effect of G-CSF on hand grip strength (c) and the diameter of rectus femoris (d)

after cardiotoxin-induced skeletal myocyte injury in csf3r$^{-/-}$ mice transplanted with the wild type bone marrow (GFP-Tg mice). e. Experimental model for bone marrow transplantation 2; bone marrow was isolated from csf3r$^{-/-}$ mice and transplanted into the wild type (csf3r$^{+/+}$) mice. f, g. Effect of G-CSF on hand grip strength (f) and the diameter of rectus femoris (g) after cardiotoxin-induced skeletal myocyte injury in the wild type mice transplanted with the csf3r$^{-/-}$ mouse bone marrow (GFP-Tg mice).

EMBODIMENTS FOR CARRYING OUT THE INVENTION

Muscle repair promotion as referred to the present invention means promoting the increase and/or division of myoblast cells in an injured muscle, with the result either that the muscle is regenerated to function in a way resembling or surpassing the inherent levels or that the pain in the muscle is reduced. The functions of muscle are contractility, flexibility, catabolic performance, and glycogen accumulation.

The muscle injury to be treated with the muscle repair promoters of the present invention is not particularly limited and may include muscle strain, muscle rupture, bruise, laceration or bite extending to the muscle, severe muscle pain (delayed muscle pain), and muscle injury from drug irritation. Muscle strain is a disease characterized by abrupt contraction of a muscle to cause partial damage of a fascia or muscle fiber. The injuries mentioned above are to be treated by the present invention irrespective of whether they occur in the muscle, muscle tissue or myoblast cells.

Specific sites of application include the belly, back, neck, finger, wrist, upper arm, shoulder, loin, breast, lower limb, knee, thigh, hamstring, the calf, etc. Muscles to be treated include biceps, triceps, femoral muscle, trapezius, gluteus maximus muscle, quadriceps, hamstrings, gastrocnemius, extensor muscle of the leg, extensor muscle of thumb, suprasupinatus, rectus abdominis muscle, adductor muscle of the thigh, extensor muscle of fingers, etc.

The muscle repair promoters of the present invention contain a granulocyte colony stimulating facto (G-CSF) as an active ingredient.

The G-CSF used as an active ingredient of the muscle repair promoters of the present invention can be any G-CSF, but preferably highly purified G-CSF, more specifically mammalian G-CSF, especially that having biological activity substantially identical to that of human G-CSF. The source from which the G-CSF is derived is not specifically limited, and naturally derived G-CSF or genetically engineered G-CSF can be used, preferably genetically engineered G-CSF. Genetically engineered G-CSF may have an amino acid sequence identical to that of naturally derived G-CSF, or may contain a deletion, substitution, addition or other modification of one or more amino acids in such amino acid sequence, so long as it has similar biological activity to that of naturally derived G-CSF. Deletion, substitution, addition or other modification of amino acids can be performed by methods known to those skilled in the art. For example, a polypeptide functionally comparable to G-CSF can be prepared by those skilled in the art by introducing an amino acid variation into G-CSF as appropriate using site-directed mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA. 82, 488-492; Kunkel (1988) Methods Enzymol. 85, 2763-2766) or other techniques. Amino acid variations also occur in nature.

Generally, an amino acid residue is preferably substituted by another amino acid in which the property of the amino acid side chain is conserved. For example, the properties of amino acid side chains include hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl-containing side chains (S, T, Y), amino acids having sulfur-containing side chains (C, M), amino acids having carboxylate- and amide-containing side chains (D, N, E, Q), amino acids having base-containing side chains (R, K, H), and amino acids having aromatic-containing side chains (H, F, Y, W) (the examples are shown by one-letter amino acid codes within each set of parentheses). It is already known that polypeptides having an amino acid sequence modified by deleting, adding and/or substituting one or more amino acid residues retain their biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Fusion proteins of G-CSF and another protein can also be used. Fusion proteins can be prepared by e.g. ligating the DNA encoding G-CSF in-frame with the DNA encoding another protein, inserting the ligation product into an expression vector, and expressing it in a host. The second protein to be fused to G-CSF herein is not specifically limited.

Chemically modified G-CSF can also be used. Examples of chemically modified G-CSF include G-CSF manipulated to have a conformational change or addition or deletion of oligosaccharide chains, and G-CSF conjugated to polyethylene glycol, vitamin B12, or a compound such as an inorganic or organic compound.

The G-CSF used in the present invention can be prepared by any process, e.g. by culturing a human tumor cell or a cell line of a human G-CSF-producing hybridoma and extracting and isolating/purifying G-CSF by various methods from the cultured cell or by producing G-CSF by genetic engineering techniques in *E.coli*, yeast, Chinese Hamster Ovary cells (CHO cells), C127 cells, COS cells, myeloma cells, BHK cells, insect cells or the like and extracting and isolating/purifying it by various methods. The G-CSF used in the present invention is preferably G-CSF prepared by genetic engineering techniques, preferably using mammalian cells (especially CHO cells) (e.g., see JPB HEI 1-44200, JPB HEI 2-5395, JPA SHO 62-129298, JPA SHO 62-132899, JPA SHO 62-236488, and JPA SHO 64-85098).

The muscle repair promoters of the present invention may, if desired, contain suspending agents, solubilizers, stabilizers, isotonizing agents, preservatives, adsorption inhibitors, surfactants, diluents, excipients, pH modifiers, soothing agents, buffers, sulfur-containing reducing agents, antioxidants, etc. as appropriate depending on the mode of administration or dosage form.

Examples of suspending agents include methylcellulose, Polysorbate 80, Polysorbate 20, hydroxyethylcellulose, gum arabic, gum tragacanth powder, sodium carboxymethylcellulose, polyoxyethylene sorbitan monolaurate, etc.

Solubilizers include polyoxyethylene hydrogenated castor oil, Polysorbate 80, Polysorbate 20, nicotinic acid amide, Macrogols, castor oil fatty acid ethyl esters, etc.

Stabilizers include dextran 40, methylcellulose, gelatin, sodium sulfite, sodium metasulfite, etc.

Isotonizing agents include e.g., D-mannitol, sorbitol, etc.

Preservatives include e.g., methyl paraoxybenzoate, ethyl paraoxybenzoate, sorbic acid, phenol, cresol, chlorocresol, etc.

Adsorption inhibitors include e.g., human serum albumin, lecithin, dextran, ethylene oxide/propylene oxide copolymers, hydroxypropylcellulose, methylcellulose, polyoxyethylene hydrogenated castor oil, polyethylene glycol, etc.

Typical examples of surfactants include:

nonionic surfactants such as ones having HLB values of 6-18, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average added ethylene oxide mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids.

Formulations of the present invention can contain one of these surfactants or more than one in combination. Preferred surfactants are polyoxyethylene sorbitan fatty acid esters such as Polysorbate 20, 40, 60 or 80, especially Polysorbates 20 and 80. Polyoxyethylene polyoxypropylene glycols typified by poloxamers (e.g. Pluronic F-68®) are also preferred.

Sulfur-containing reducing agents include e.g., N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms.

Antioxidants include e.g., erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfate, sodium sulfite, triamyl gallate, propyl gallate or chelating agents such as disodium ethylenediamine tetraacetate (EDTA), sodium pyrophosphate, and sodium metaphosphate.

Other components commonly added may also be contained, e.g., inorganic salts such as sodium chloride, potassium chloride, calcium chloride, sodium phosphate, potassium phosphate, and sodium bicarbonate; and organic salts such as sodium citrate, potassium citrate, and sodium acetate.

The muscle repair promoters of the present invention can be administered in a dosage form suitable as injectables for local administration (e.g., subcutaneous, intradermal or intramuscular administration). Intramuscular administration is particularly preferred as local administration.

To prepare injectables, the components described above are dissolved in an aqueous buffer known in the field of solution formulations such as a phosphate buffer (preferably sodium monohydrogen phosphate–sodium dihydrogen phosphate system) and/or a citrate buffer (preferably sodium citrate buffer) and/or an acetate buffer to thereby prepare a solution formulation. The concentration of the buffer is normally 1-500 mM, preferably 5-100 mM, more preferably 10-20 mM. Injectables may be solution formulations or freeze-dried formulations.

The timing of administration of the muscle repair promoters the present invention which contain G-CSF as an active ingredient can be determined as appropriate by those skilled in the art with consideration given to the condition of the patient to be treated, but the promoters are preferably administered at 2-10 days after muscle injury, more preferably at 3-8 days after muscle injury, and most preferably at 4-7 days after muscle injury.

The muscle repair promoters of the present invention are preferably administered at an interval of 4 days, more preferably at an interval of 3 days, and most preferably at an interval of 2 days.

The muscle repair promoters of the present invention were verified to be adequately effective in mice upon local administration, even when the dosage was as low as 0.5 μg/body (ca. 21 μg/kg) (Example 5). Generally, the effect of human G-CSF in human is about 20 times greater than in mouse. For example, it is known that in humans, stem cells are recruited and WBC also increase when human G-CSF is continuously administered at a dose of 10 μg/kg (Br J Hematol Watts 1997 98 474-479). In mice, on the other hand, it was confirmed that the number of peripheral neutrophils increased when human G-CSF was administered at a dose of 200 μg/kg for 5 days (Blood 89:2736, 1997) whereas WBC increased when the mice were administered with human G-CSF at a dose of 250 μg/kg for 5 days (Blood, 1997 May 1:89(9):3186-91). Hence, in order that the muscle repair promoters of the present invention attain the intended muscle repair effect while causing less side-effect in human, the dose of single administration is preferably 0.1-10 μg/kg, more preferably 0.5-5 μg/kg, and most preferably 1-2.5 μg/kg. The total dosage to be administered over the period prescribed above is preferably 0.2-50 μg/kg, more preferably 1.0-25 μg/kg, and most preferably 2.0-12.5 μg/kg.

It should, however, be noted that the present invention is by no means limited by the dosage of human G-CSF.

The muscle repair promoters of the present invention may be used in combination with other drugs.

Consideration of the Underlying Mechanism of the Invention

Although not intending to be bound by any particular theory, the present inventors consider the underlying mechanism of the present invention as follows.

It has been confirmed according to the present invention that in skeletal myocyte development and regeneration, G-CSF and G-CSFR have a pivotal role as mediated by the proliferation of myoblasts. Interestingly, this mechanism is conserved between embryonic skeletal myocyte development and adult skeletal myocyte regeneration. G-CSFR is transiently but strongly expressed in myoblasts proliferating in the developing somite. G-CSFR knockout mice experienced a decrease in the diameter of rectus femoris muscle, which means G-CSF and G-CSFR signaling is essential for the proper skeletal muscle development. G-CSFR is also expressed in the regenerating adult myocyte. G-CSF stimulates these G-CSFR expressing myoblasts and promotes skeletal muscle regeneration after skeletal muscle injury. The G-CSFR knockout mice experienced an impairment of the skeletal muscle regeneration which is spontaneous. G-CSF is a famous hematopoietic cytokine and can recruit hematopopietic cells. In order to exclude the possible involvement of the effects of the hematopoietic cells on skeletal muscle regeneration following G-CSF injection, wild type bone marrow was transplanted to G-CSFR knockout mice. In these mice, skeletal myocytes did not express G-CSFR while hematopoietic cells expressed G-CSFR and showed a normal response to G-CSF. If hematopoietic cells contributed to the skeletal muscle regeneration, these mice would show the normal regeneration abilities. However, these bone marrow transplanted G-CSFR knockout mice did not show any improvement in skeletal muscle regeneration upon administration of G-CSF.

G-CSF recruits hematopoietic cells from bone marrow to the peripheral circulation. The contribution of bone marrow cells to regenerating muscle has been documented (e.g., Ferrari, G. et al. Muscle Regeneration by Bone Marrow-Derived Myogenic Progenitors. Science 279, 1528-1530, doi: 10.1126/science.279.5356.1528 (1998)). Hence, the present inventors made a study to determine whether G-CSF would be dependent on bone marrow cells in the process of skeletal muscle regeneration and clearly showed that G-CSFR expressing bone marrows transplanted into G-CSFR knockout mice in no way contributed to skeletal muscle regeneration. As a result, the present inventors confirmed that the effect of G-CSF on skeletal muscle was a direct action on skeletal muscle cells. Clinically, G-CSF is used in patients with neutropenia resulting from immunosuppressive chemotherapy, severe congenital neutropenia or life-threatening bacterial infection, as well for harvesting stem cells. Myalgia (muscle pain) is one of the main side-effects of G-CSF that should be noted when it is administered to human (Taylor, K. M. et al. Recombinant human granulocyte colony-stimulating factor hastens granulocyte recovery after high-dose chemotherapy and autologous bone marrow transplantation in Hodgkin's disease [published erratum appears in J Clin Oncol 1990 March;8(3):567]. J Clin Oncol 7, 1791-1799 (1989)). A mechanism that can be speculated for this phenomenon is that G-CSF injection stimulates skeletal myoblasts and the resulting explosive proliferation of skeletal myocytes gives rise to myalgia. From several aspects on past clinical usage of G-CSF, its safety and side effects have been precisely surveyed. The results of the present invention provide a new therapeutic potential and mechanistic insight of G-CSF on skeletal muscle development and regeneration and this is expected to accelerate the application of G-CSF in skeletal muscle regeneration therapy.

The following examples further illustrate the present invention but they are no by means intended to limit the scope of the invention. Various changes and modifications can be made by those skilled in the art on the basis of the description herein, and such changes and modifications are also included in the present invention.

EXAMPLES

The following are the experimental methods used in the Examples.

Whole-mount in situ Hybridization

Murine embryos were removed from the wild-type ICR pregnant mice at embryonic day 10.5. Whole-mount in situ hybridization was performed as described (Non-patent document 4). The full-length cDNAs for murine c-met, pax3, myod, and mrf4 (accession numbers NM_008591, NM_001159520, NM_010866, NM_008657) were kindly provided from Prof. M. E. Buckingham (Department of Developmental Biology, Pasteur Institute). The full-length cDNAs for murine csf3r (accession number NM_007782) was kindly provided from Prof. S. Nagata (Department of Genetics, Osaka University) (Fukunaga, R., Seto, Y., Mizushima, S. & Nagata, S. Three Different mRNAs Encoding Human Granulocyte Colony-Stimulating Factor Receptor. Proceedings of the National Academy of Sciences 87, 8702-8706, doi:10.1073/pnas.87.22.8702 (1990)). The probes were generated using T3 or T7 RNA polymerase.

Myf5 NlacZ Mice

Myf5 nlacZ mice were a kind gift from Dr. Shahragim Tajbakhsh (Dept. of Developmental Biology, Pasteur Institute) (Tajbakhsh, S., Rocancourt, D. & Buckingham, M. Muscle progenitor cells failing to respond to positional cues adopt non-myogenic fates in myf-5 null mice. Nature 384, 266-270 (1996)).

Immunofluorescence

Murine embryos on embryonic days 8.5, 9.5, 10.5, 11.5 and 12.5 were fixed in 4% paraformaldehyde for 3 hours and embedded for frozen sectioning using Tissue-Tek OCT (Sakura Finetek, Chuo-ku, Tokyo). The samples were incubated with Triton X-100 for 5 minutes at room temperature, then washed and incubated with the following primary antibodies: anti-G-CSF receptor (Santa Cruz Biotechnology (sc-9173), 1:50), anti-pax3 (ATCC, 1:200), anti-Pax7 (R&D SYSTEMS (MAB1675), 1:50), anti-MyoD (DAKO (M3512), 1:50), anti-Myogenin (Santa Cruz Biotechnology (sc-12732), 1:50), anti-Desmin (Dako (M0760), 1:200), anti-G-CSF (Santa Cruz Biotechnology (sc-9351), 1:50), anti-α-Actinin (SIGMA (A7811), 1:1000), and anti-GAPDH (Santa Cruz Biotechnology (sc-20357), 1:200), all antibodies being purchased. After overnight incubation, the bound antibodies were visualized with a secondary antibody conjugated to Alexa 488 or Alexa 546 (Molecular Probes, Minato-ku, Tokyo). Nuclei were stained with 4',6-diamidine-2-phenylindole dihydrochloride (DAPI; Invitrogen (D21490)). For BrdU staining, BrdU labeling kit (1296736, Roche, Basel, Switzerland) was used. After antigen retrieval using histoVT One (L6F9587 Nacalai Tesque, Nakagyo-ku, Kyoto) and subsequent blocking, BrdU was stained as described in the protocol.

C2C12 Cell Culture

C2C12 mouse myoblasts (ATCC) were cultured in DMEM/10% FBS (GIBCO). In the differentiation condition, the medium was replaced with DMEM/2% horse serum (GIBCO) for differentiation. Recombinant murine G-CSF (414-CS, R&D Systems, Minneapolis, Minn.) was added on prescribed days. Signal inhibition analysis was performed by administering G-CSFR neutralizing antibody (AF-414-NA, R&D Systems).

Western Blotting

C2C12 cells were treated with G-CSF. Cell extracts were isolated at 0, 5, 10, 15, 30, 45 and 60 minutes after G-CSF stimulation. Protein lysates were resolved by SDS-PAGE and transferred to a PVDF membrane. Subsequently, immunoblotting was performed with anti-phospho STAT3 (9131), anti-phospho AKT (9271), anti-phospho ERK (9101), anti-phospho JNK (9251S), and anti-phospho p38MAPK (9211S) antibodies (all purchased from Cell Signaling TECHNOLOGY, Beverly, Mass.), and horseradish peroxidase-conjugated anti IgG, followed by development with the SuperSignal West Pico Chemiluminescent reagent (Pierce, Rockford, Ill.). Same membrane was retrieved and re-blotted with anti-STAT3 (9132), anti-AKT (9272), anti-ERK (9102), anti-JNK (9252), and anti-p38MAPK (9212) antibodies (all purchased from Cell Signaling TECHNOLOGY), respectively.

Luciferase Analysis

C2C12 cells cultured in DMEM were transfected with Lipofectamine (Invitrogen) according to the manufacturer's instructions. APRE luciferase plasmid was kindly provided from Prof. Yoshimura (Department of Immunology, Keio University). One hundred nanograms of APRE reporter was used. The G-CSF administration doses represented by the ramp symbol indicate 37.5, 125, and 375 µg/ml, respectively. CMV-Renilla luciferase was used as an internal control, to normalize for variations in transfection efficiency. All the proteins were expressed at very similar levels, as confirmed by Western blotting.

Animal Experiment

All experimental procedures and protocols were approved by the Animal Care and Use Committee of Keio University and conformed to the NIH *Guidelines for the Care and Use of Laboratory Animals*.

Skeletal Muscle Injury Model

Cardiotoxin (*Naja mossambica mossambica*, 10 µM; Sigma-Aldrich, St. Louis, Mo.) diluted in 100 µl of PBS was injected at a dose of 100 µl into rectus femoris of BL6/J mice using a 27-gauge needle and a 1-ml syringe. The needle was inserted deeply into the rectus femoris longitudinally from the knee. Cardiotoxin was injected along the length of the muscle. Mice in a control group were injected with 100 µl of PBS. Mice (treated and control groups) were sacrificed at various time points after cardiotoxin injection, and blood samples (1.0-1.5 ml from each mouse) were collected in heparin-rinsed syringes.

$Csf3r^{-/-}$ Mice $Csf3r^{-/-}$ mice were a kind gift from Dr. Daniel C. Link (Washington University School of Medicine, St. Louis) (Richards, M. K., Liu, F., Iwasaki, H., Akashi, K. & Link, D. C. Pivotal role of granulocyte colony-stimulating factor in the development of progenitors in the common myeloid pathway. Blood 102, 3562-3568, doi:10.1182/blood-2003-02-0593 (2003)).

Hand Grip Strength Meter Test

There were 5 training sessions during which animals were held, facing the bar of the Grip Strength Meter (GSM, Muromachi Kikai Co., Ltd., Tokyo, Japan), and the forearms of each animal were gently restrained by the experimenter. When their unrestrained forepaws were brought into contact with the bar of the GSM, the animals were allowed to grip the bar and then gently pulled away from the device. Then, the GSM measured the maximal force before the animal released the bar.

Bone Marrow Transplantation

Bone marrow (BM) cells were harvested from 8-week-old EGFP-transgenic mice. After irradiation with a single dose of 9.0 Gy, the unfractionated $EGFP^+$ BM cells ($1\times10^6$ cells) were injected via the tail vein. To assess chimerism, peripheral blood cells were collected from the recipient mice 8 weeks after BM transplantation and erythrocytes were eliminated by hemolysis with ammonium chloride; thereafter, the frequency of $EGFP^+$ cells among peripheral nucleated blood cells was determined with a fluorescence-activated cell sorter (Becton Dickinson, San Jose, Calif.)

Statistical Analysis

Data were analyzed using StatView J-4.5 software. Values are reported as means ±SD. Comparisons amongst groups were performed by one-way ANOVA. Scheffe's F test was used to determine levels of significance. The probability level accepted for significance was $P<0.05$.

Example 1

The expression pattern of csf3r in developing mouse embryo was investigated by whole-mount in situ hybridization.

Figure 1:
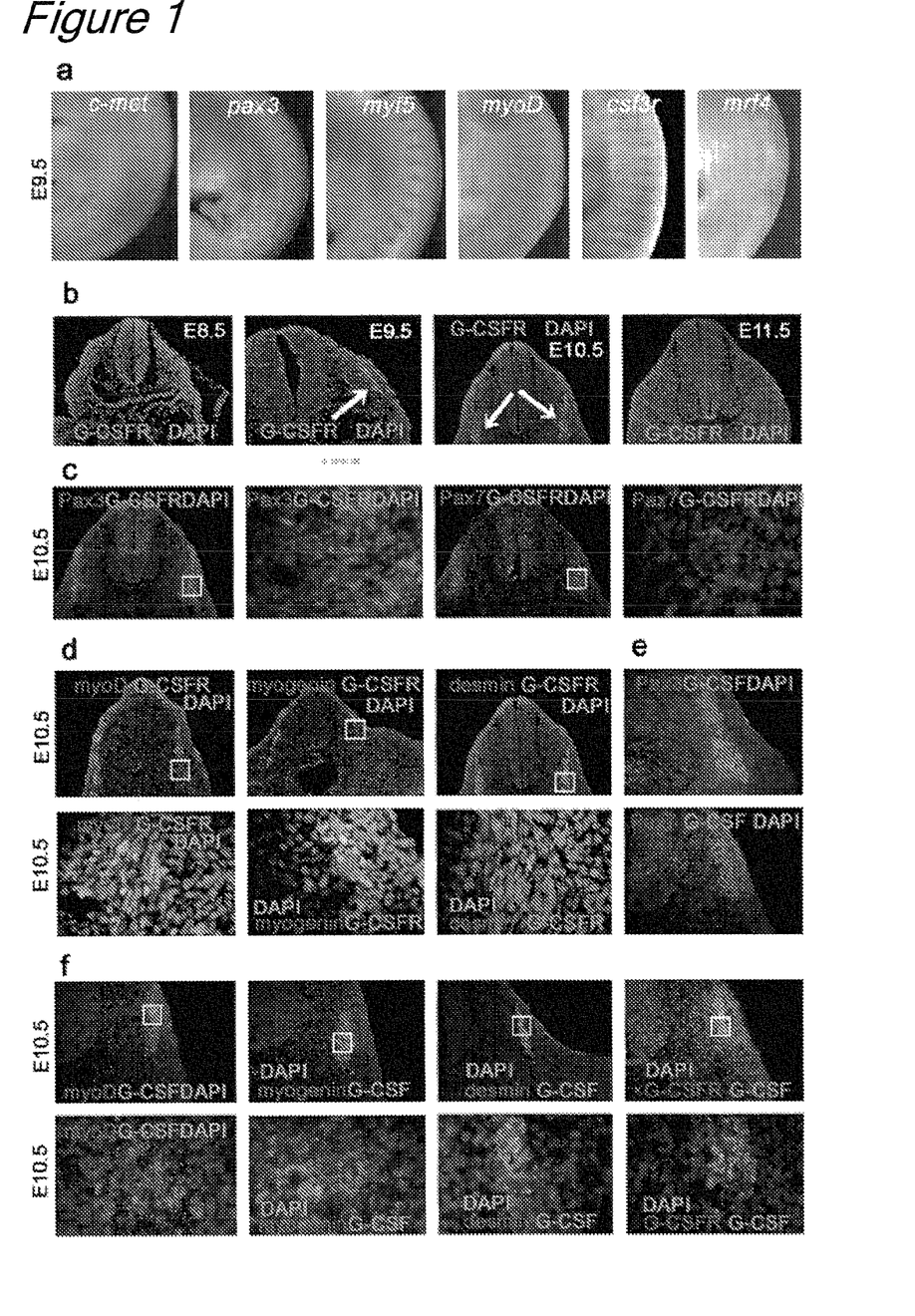

In order to clarify where in the somites csf3r was expressed, several markers for skeletal myocyte differentiation were compared (FIG. 1a). C-met which encodes a tyrosine kinase receptor for hepatocyte growth factor (HGF) is expressed in the dermomyotome and essential for the delamination/migration of muscle progenitor cells. The expression of C-met was restricted to the ventral portion of somites and the expression pattern of csf3r was not similar to that of c-met (Yang, X. M., Vogan, K., Gros, P. & Park, M. Expression of the met receptor tyrosine kinase in muscle progenitor cells in somites and limbs is absent in Splotch mice. Development 122, 2163-2171 (1996)). Skeletal myocyte development is tuned finely by myogenic transcription factors. Pax3 is first expressed in the presomitic mesoderm and expressed in the somitic epithelium of the dermomyotome. The expression of Pax3 and Pax7 is then repressed as dermomyotome-derived cells activate myogenic transcription factors. The expression pattern of Pax3 was not identical to that of csf3r. The myogenic bHLH genes also show unique expression patterns in differential skeletal muscle developmental stage. MyoD and myf5 are expressed in undifferentiated proliferating myoblasts (Tapscott, S. J. et al. MyoD1: a nuclear phosphoprotein requiring a Myc homology region to convert fibroblasts to myoblasts. Science 242, 405-411, doi: 10.1126/science.3175662 (1988); Sara J. Venters, S. v. T. t. M. J. D. Early development of the myotome in the mouse. Developmental Dynamics 216, 219-232 (1999)) whereas mrf4 is not expressed until late in the differentiation program (Rhodes, S. J. & Konieczny, S. F. Identification of MRF4: a new member of the muscle regulatory factor gene family. Genes & Development 3, 2050-2061, doi:10.1101/gad.3.12b.2050 (1989); Bober, E. et al. The muscle regulatory gene, Myf-6, has a biphasic pattern of expression during early mouse development. J. Cell Biol. 113, 1255-1265, doi: 10.1083/jcb.113.6.1255 (1991)). Compared to those marker expression patterns, the expression pattern of csf3r resembled those of myf5 and MyoD. Late differentiation marker mrf4 was not identical to that of csf3r.

Immunofluoresent staining of sections of embryos in the differential developing stage demonstrated that the expression of G-CSFR in the somite was restricted the period of E9.5 to E10.5. Before E9.5, G-CSFR was not observed in somite, and after E11.5, G-CSFR expression disappeared (FIG. 1b).

The foregoing results suggested that G-CSF might be involved in the development of undifferentiated proliferating myoblasts.

Example 2

Skeletal myocyte premature and mature markers in several differentiation stages were immunostained to reveal what stage of skeletal myocyte would express the G-CSFR. Skeletal muscle progenitor cells arise in the central part of the dermomyotome, coexpress Pax3 and Pax7, and can differentiate into skeletal muscle fibers during embryogenesis (Messina, G. & Cossu, G. The origin of embryonic and fetal myoblasts: a role of Pax3 and Pax7. Genes & Development 23, 902-905, doi:10.1101/gad.1797009 (2009)). Pax3 and Pax7 have partially overlapping and partially unique functions in myogenic progenitors and they are both down-regulated during myogenic differentiation, following myogenic regulatory factor (MRF) expression. Pax3 and Pax7 expressing myogenic progenitor cells did not express G-CSFR (FIG. 1c). However, among the cells in which Pax3 and Pax7 diminished, those which started to express MyoD and Myogenin showed G-CSFR expression (FIG. 1d). As in the previous report about G-CSFR expression pattern, the immunoreactivity for G-CSFR was localized to the cell membrane and cytoplasm under steady-state conditions (Aarts, L. H. J., Roovers, O., Ward, A. C. & Touw, I. P. Receptor activation and 2 distinct COOH-terminal motifs control G-CSF receptor distribution and internalization kinetics. Blood 103, 571-579, doi:10.1182/blood-2003-07-2250 (2004)). These cells also expressed desmin, an intermediate filament expressed in skeletal muscles.

G-CSF, or the ligand of C-CSFR, was also examined by immunostaining. G-CSF expression was not detected in Pax3 and Pax7 expressing myogenic progenitor cells (FIG. 1e). As in the case of G-CSFR expressing cells, among the cells in which Pax3 and Pax7 diminished, those which started to express MyoD and Myogenin also showed G-CSF expression (FIG. 1f). Double immunostaining for G-CSF and G-CSFR revealed that G-CSFR expressing cells also expressed G-CSF. These results revealed that the cells undergoing early differentiation into skeletal myocytes have a G-CSF signalling in an autocrine fashion.

The above-described experiment verified that the G-CSF and G-CSF receptor are expressed in differentiating skeletal myocytes.

Example 3

To elucidate the role of G-CSF in myogenic cells, myoblast cells were analyzed in vitro.

The G-CSF and anti-G-CSF neutralizing antibody were added at the following timings and concentrations.

G-CSF

Figure 2:
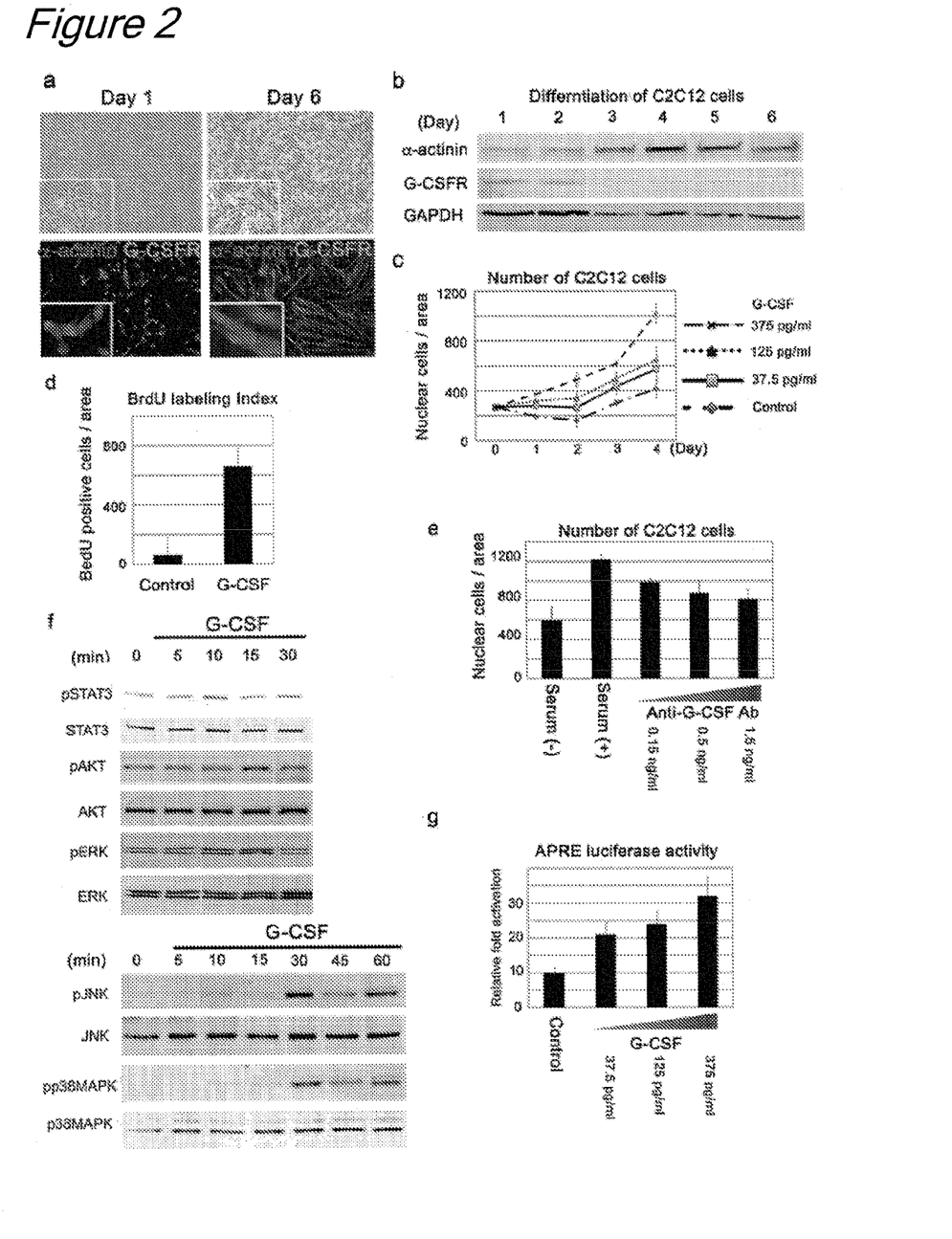

Timing of addition: One day after seeding, cells were adhered to a dish by means of DMEM+10% FBS and on the second day, the culture was washed and DMEM (control) and DMEM+G-CSF were administered (this second day is designated as Day 0 in FIG. 2c and the administration was effected only singly at Day 0.)

Concentration of G-CSF added: Values were 0 µg/ml, 37.5 µg/ml, 125 82 g/ml and 375 µg/ml from bottom to top in the graph of FIG. 2c.

Anti-G-CSF Neutralizing Anti Body

Timing of addition: One day after seeding, cells were adhered to a dish by means of DMEM+10% FBS and on the second day, the culture was washed and DMEM (Serum), DMEM+0.1% HS (Serum+) and DMEM+0.1%HS+anti-G-CSF neutralizing antibody were administered (this second day is designated as Day 0 in FIG. 2e and the administration was effected only singly at Day 0.)

Concentration of anti-G-CSF neutralizing antibody: 0.15 ng/ml, 0.5 ng/ml, and 1.5 ng/ml.

C2C12 cell line is a subclone of C2 cells established from the regenerating thigh muscle of an adult mouse and widely used as a myoblast cell line (Blau, H. M., Chiu, C.-P. & Webster, C. Cytoplasmic activation of human nuclear genes in stable heterocaryons. Cell 32, 1171-1180 (1983)). In low serum culture conditions, C2C12 cells fuse each other and differentiate into multinucleated myotubes (FIG. 2a). Immunstaining for G-CSFR and □α-actinin revealed that premature C2C12 cells expressed G-CSFR but not actinin, while mature fused myotubes clearly expressed α-actinin but α-actinin positive cells never expressed G-CSFR. Western blot analysis confirmed that as differentiation proceeded, α-actinin expression was gradually increased and G-CSFR was decreased (FIG. 2b).

In order to clarify the role of G-CSF on myocyte, G-CSF was administrated into C2C12 cells when G-CSFR was expressed. G-CSF administration significantly increased the number of C2C12 cells in a dose-dependent manner (FIG. 2c). At day 0, G-CSF was administered in an amount of 375 µg/ml which was the maximum dose used in the experiment the results of which are shown in FIG. 2c, and measurement was conducted at Day 4. A BrdU incorporation experiment also revealed that the increased cell number was attributed to cell proliferation by G-CSF (FIG. 2d). In addition, a neutralizing antibody was used to inhibit innate G-CSF signaling so as to determine whether G-CSF was essential for the proliferation of C2C12 cells. Neutralizing antibody for G-CSF inhibited the serum-dependent proliferation of C2C12 cells (measurement conducted at Day 4) (FIG. 2e).

The binding of G-CSF to its receptor has been reported to activate various signals including ERK, JNK, p38MAPK, AKT, and STAT (signal transducer and activator of transcription) proteins in hematopoietic cells (Avalos, B. Molecular analysis of the granulocyte colony-stimulating factor receptor. Blood 88, 761-777 (1996)). The present inventors confirmed that G-CSF activated STAT3, AKT, ERK, JNK and p38MAPK in C2C12 cells in a time-dependent manner. In the experiment under consideration, G-CSF was added in an amount of 375 µg/ml (FIG. 2f). Among the substances mentioned above, STAT3 has been reported to contribute to the proliferation of myocyte progenitor cells (Serrano, A. L., Baeza-Raja, B., Perdiguero, E., Jardi, M. & Munoz-Canoves, P. Interleukin-6 is an essential regulator of satellite cell-mediated skeletal muscle hypertrophy. Cell Metab 7, 33-44 (2008); Lynn A. Megeney, Robert L. S. Perry, Jennifer E. Lecouter & Michael A. Rudnicki. bFGF and LIF signaling activates STAT3 in proliferating myoblasts. Developmental Genetics 19, 139-145 (1996)). G-CSF administration into the C2C12 cell culture medium increased the activity of APRE luciferase which responds to STAT3 activation (measurement conducted at Day 1) (FIG. 2g). These results clearly showed that G-CSF promoted the proliferation in C2C12 myoblasts as mediated by G-CSFR.

Example 4

An investigation was made to see whether G-CSFR would be expressed in skeletal myocytes in the process of regeneration after injury. Cardiotoxin is known to damage the plasma membrane of myofibers but leave basal lamina, satellite cells, and nerves intact, allowing rapid and reproducible muscle regeneration (Hosaka, Y. et al. {alpha}1-Syntrophin-deficient skeletal muscle exhibits hypertrophy and aberrant formation of neuromuscular junctions during regeneration. J. Cell Biol. 158, 1097-1107, doi:10.1083/jcb.200204076 (2002)).

Figure 3:
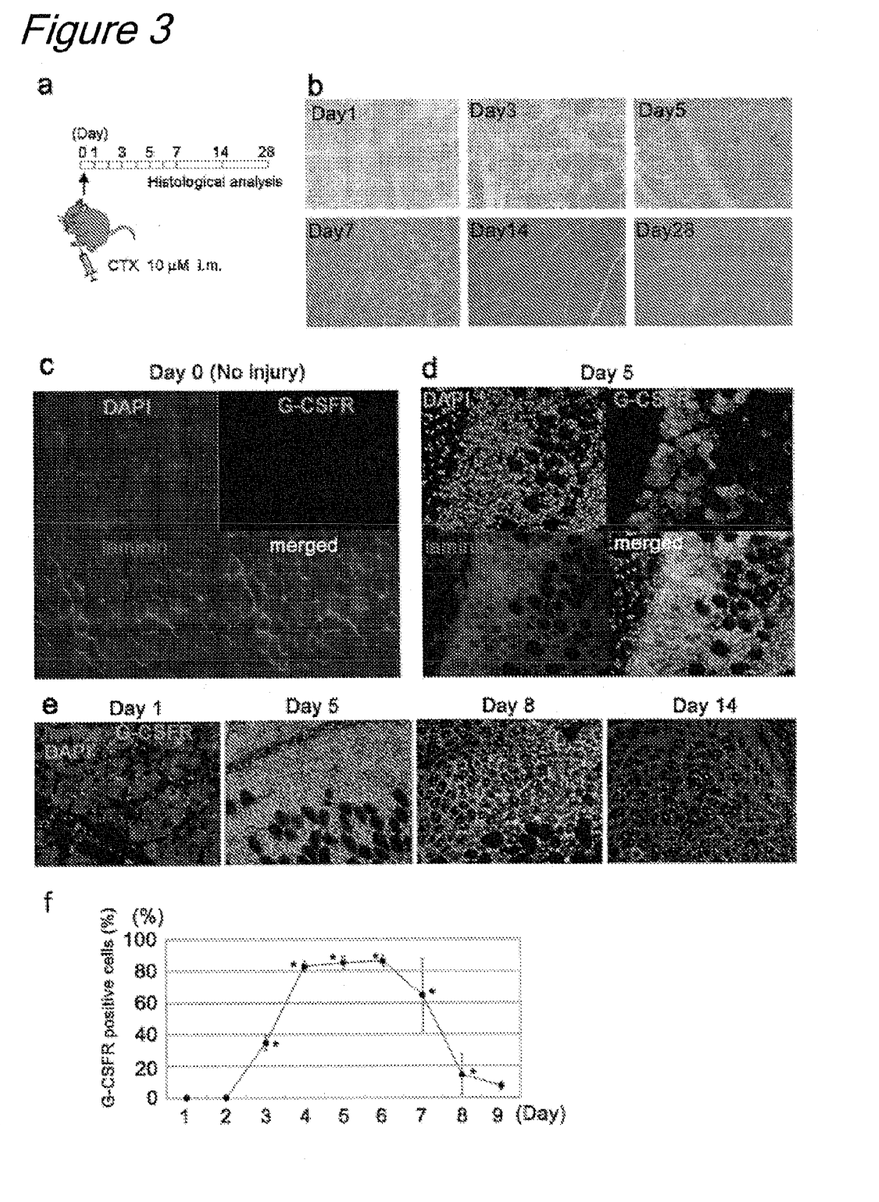

The present inventors directly injected cardiotoxin into the femoral muscles, and performed histological analyses serially up to day 28 (FIG. 3a). After cardiotoxin injection, spontaneous regeneration of the injured muscle was observed (FIG. 3b). Starting at day 1 or 2, a number of inflammatory cells infiltrated into the injured muscle and the injured myotubes were absorbed. The satellite cells or TA cells (transit amplifying cells) began to increase at day 3, and central nuclear early myocytes were clearly identified starting at day 5. They fused each other and their diameter rapidly increased thereafter. Starting at day 7, the injured area was filled with the regenerated myotubes which had center nuclei and were smaller in diameter than mature myotubes. Starting at day 28, the regenerated myotubes were substantially equal in diameter to the non-injured myotubes, though they had center nuclei.

As the result of triple-immunostaining for laminin, G-CSFR and DAPI, G-CSFR-positive cells were not observed in the non-injured skeletal muscle (FIG. 3c). In contrast, G-CSFR was clearly expressed in the regenerating myocytes at day 5 after cardiotoxin injection (FIG. 3d). The size of the G-CSFR positive cells was apparently larger than that of infiltrated inflammatory cells, and they were round shape, central nuclear, and completely surrounded by laminin, indicating that they were regenerating early myocytes which expressed G-CSFR. Serial immunofluorescent staining analyses demonstrated that G-CSFR expressing cells were observed only at days 3 to 8 after skeletal myocyte injury (FIGS. 3e and 3f).

Muscle repair is characterized by discrete stages of regeneration. In this process, skeletal muscle regeneration proceeds which comprises the activation of satellite cells, as well as the proliferation, differentiation, and maturation of satellite cells or TA cells (Shi, X. & Garry, D. J. Muscle stem cells in development, regeneration, and disease. Genes & Development 20, 1692-1708, doi:10.1101/gad.1419406 (2006)). The day of G-CSFR expression corresponded to the day at which skeletal muscle progenitor cells proliferated.

Example 5

In order to elucidate the action of G-CSF on regenerating skeletal myocyte, G-CSF was injected into models of cardiotoxin-induced skeletal muscle injury. G-CSF was administered intravenously or directly injected into the injured muscle at days 4 and 6 when G-CSFR was strongly expressed, and at day 7 skeletal muscle regeneration was observed. Final concentration of addition: A 100-µl portion was administered at respective concentrations of 0 µg/ml, 5 µg/ml, and 50 µg/ml. Timing, route, frequency, and site of administration: With Day 0 being assigned as the day when skeletal muscle was injured, the test substance was injected into the tail vein and locally injected into the injured rectus femoris at Days 4 and 6.
Number of experimental animals: n=5
Average weight of mice: 24.1 g The anti-G-CSF neutralizing antibody was locally administered to the rectus femoris in a single dose at Day 3 under the same conditions as with human G-CSF.

Figure 4:
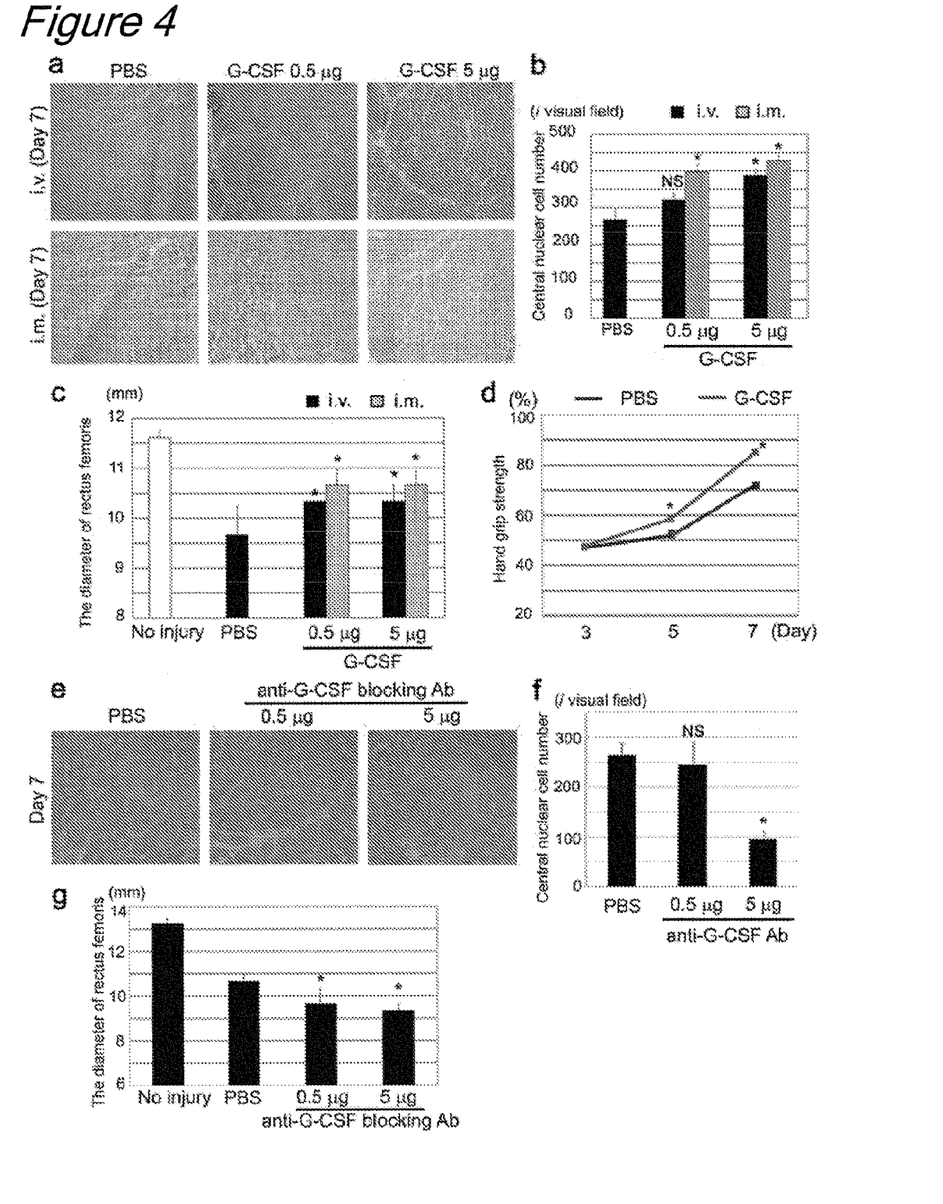

In the higher G-CSF administration dosage, intravenous administration was effective for skeletal muscle regeneration in comparison with PBS administration. Intramuscular administration was more effective than intravenous administration in the lower G-CSF administration dosage (FIG. 4a). The central nuclear cells represent the regenerated skeletal myocytes (Shi, X. & Garry, D. J. Muscle stem cells in development, regeneration, and disease. Genes & Development 20, 1692-1708, doi:10.1101/gad.1419406 (2006)). The number of the central nuclear cells was significantly increased by G-CSF administration and intramuscular G-CSF administration significantly augmented skeletal muscle regeneration (FIG. 4b). The diameter of injured muscle was measured to show that G-CSF administration significantly increased the diameter of the regenerated muscle. The diameter of rectus femoris was also increased by intramuscular administration and the increase was more prominent than by intravenous administration (FIG. 4c). Functional recovery was assessed by measurement of hand grip strength; G-CSF (100 µl administered at a concentration of 50 µg/ml) significantly improved the functional recovery at 5 and 7 days after skeletal muscle injury as compared with PBS administration (FIG. 4d).

To determine whether innate G-CSF signaling was necessary for proper skeletal myocyte regeneration, the anti-G-CSF neutralizing antibody was administrated after cardiotoxin-induced skeletal muscle injury. The anti G-CSF neutralizing antibody deteriorated the spontaneous skeletal myocyte regeneration in a manner dependent on the dose of its administration (FIG. 4e). Central nucleatr cells representing the regenerating myocytes were drastically deceased by the addition of the anti-G-CSF neutralizing antibody (FIG. 4f). The diameter of the injured muscle was also significantly decreased by the administration of the anti-G-CSF neutralizing antibody as compared with the administration of PBS (FIG. 4g). These results clearly showed that exogenous G-CSF augments skeletal myocyte regeneration and that physiological innate G-CSF signaling plays an essential role for the proper skeletal myocyte regeneration.

It was also found that the administration of human G-CSF is effective in regenerating skeletal myocytes even at the lower dosage and that intramuscular administration is more effective than intravenous adminisdration.

Example 6

Figure 5:
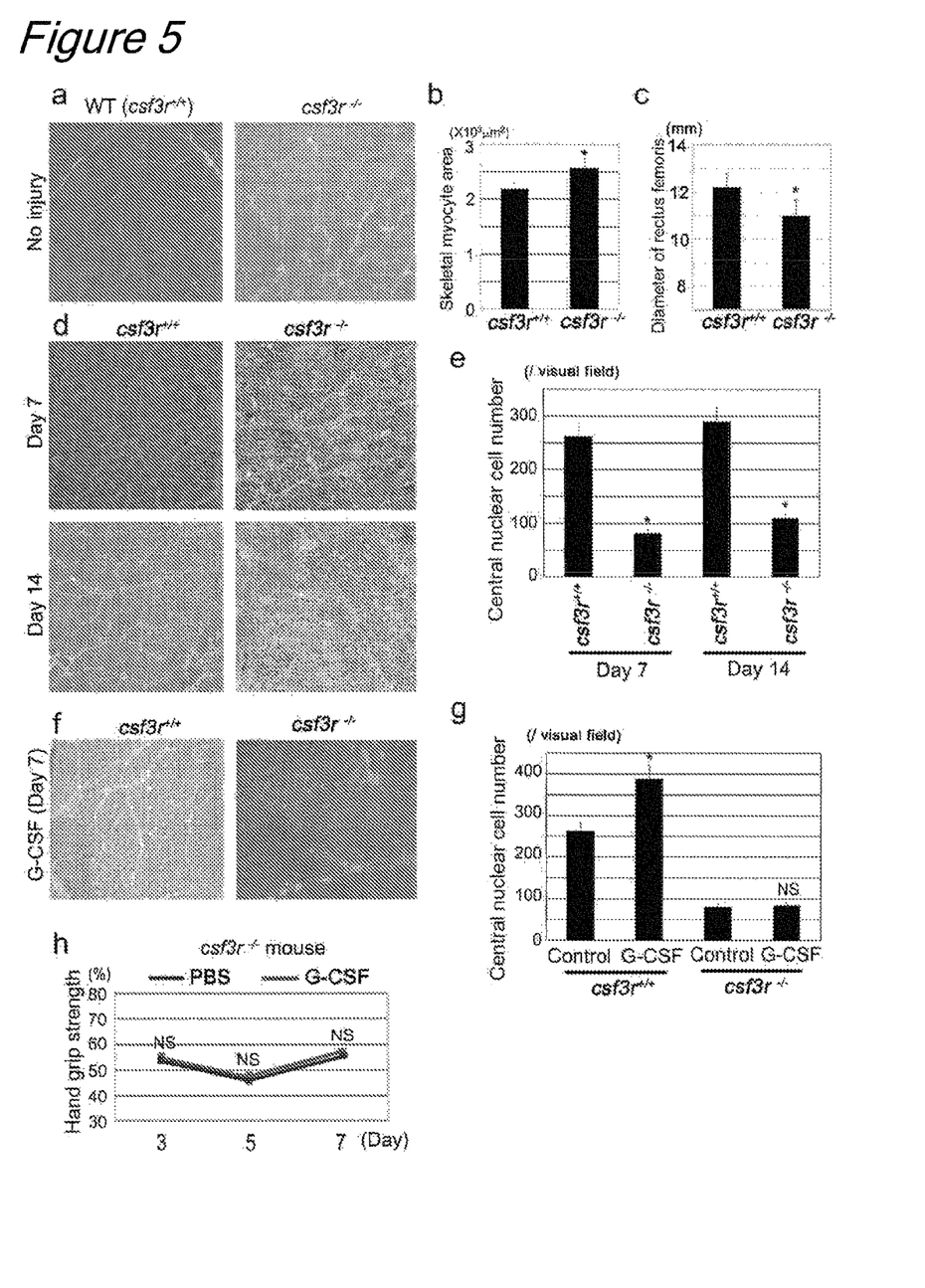

In order to clarify the role of G-CSF and G-CSF receptor signaling in skeletal myocytes, G-CSFR knockout (csf3r$^{-/-}$) mice that had G-CSF signaling inactivated genetically were examined. The csf3r$^{-/-}$ mice were used mainly for examination in hematological aspects. The number of delivered mice in the csf3r$^{-/-}$ mice was small and approximately half the number of delivered mice in the wild type (csf3r$^{+/+}$) mice. Normally delivered csf3r$^{-/-}$ mice showed no significant difference in appearance. When they were fully grown up, their body size was slightly but significantly smaller than that of csf3r$^{+/+}$. Apparently, histological analysis of csf3r$^{-/-}$ mouse's skeletal muscle revealed no significant difference compared with the csf3r$^{+/+}$ mice (FIG. 5a). However, when sections of skeletal muscle were examined, each myocyte was slightly but significantly larger in the csf3r$^{-/-}$ mice than in the csf3r$^{+/+}$ mice (FIG. 5b). On the other hand, the diameter of rectus femoris was significantly smaller than in the wild type (FIG. 5c). These findings suggested that in the csf3r$^{-/-}$ mouse, skeletal muscle proliferation deteriorates in developmental stage and each skeletal myocyte becomes hypertrophic in compensation.

To determine whether innate G-CSFR was necessary for proper skeletal myocyte regeneration, csf3r$^{-/-}$ mice were subjected to cardiotoxin-induced skeletal muscle injury. The csf3r$^{-/-}$ mice deteriorated in skeletal muscle regeneration at days 7 and 14 after caridotoxin-induced injury (FIG. 5d). The number of central nuclear myocytes in the regenerating skeletal muscle was significantly decreased in the csf3r$^{-/-}$ mice, suggesting that G-CSFR was essential for the skeletal muscle regeneration (FIG. 5e). To confirm that the action of G-CSF was mediated by G-CSFR, G-CSF was administrated to the csf3r$^{-/-}$ mice. To be more specific, G-CSF was locally administrated (100 µl each at a concentration of 50 µg/ml) to the injured rectus femoris at days 4 and 6. If G-CSF acts via another receptor, G-CSF should also improve the skeletal muscle regeneration in csf3r$^{-/-}$ mice but an administration of the exogenous G-CSF was unable to improve the skeletal muscle regeneration (FIG. 5f). The number of central nuclear myocytes in the regenerating skeletal muscle was measured to show that the administration of G-CSF significantly increased the diameter of the regenerated muscle in the csf3r$^{+/+}$ mice but that it was not effective in the csf3r$^{-/-}$ mice (FIG. 5g). Functional recovery was assessed by measurement of hand grip strength; even when G-CSF was administered, no functional recovery was recognized at 5 and 7 days after skeletal muscle injury (FIG. 5h).

Example 7

Figure 6:
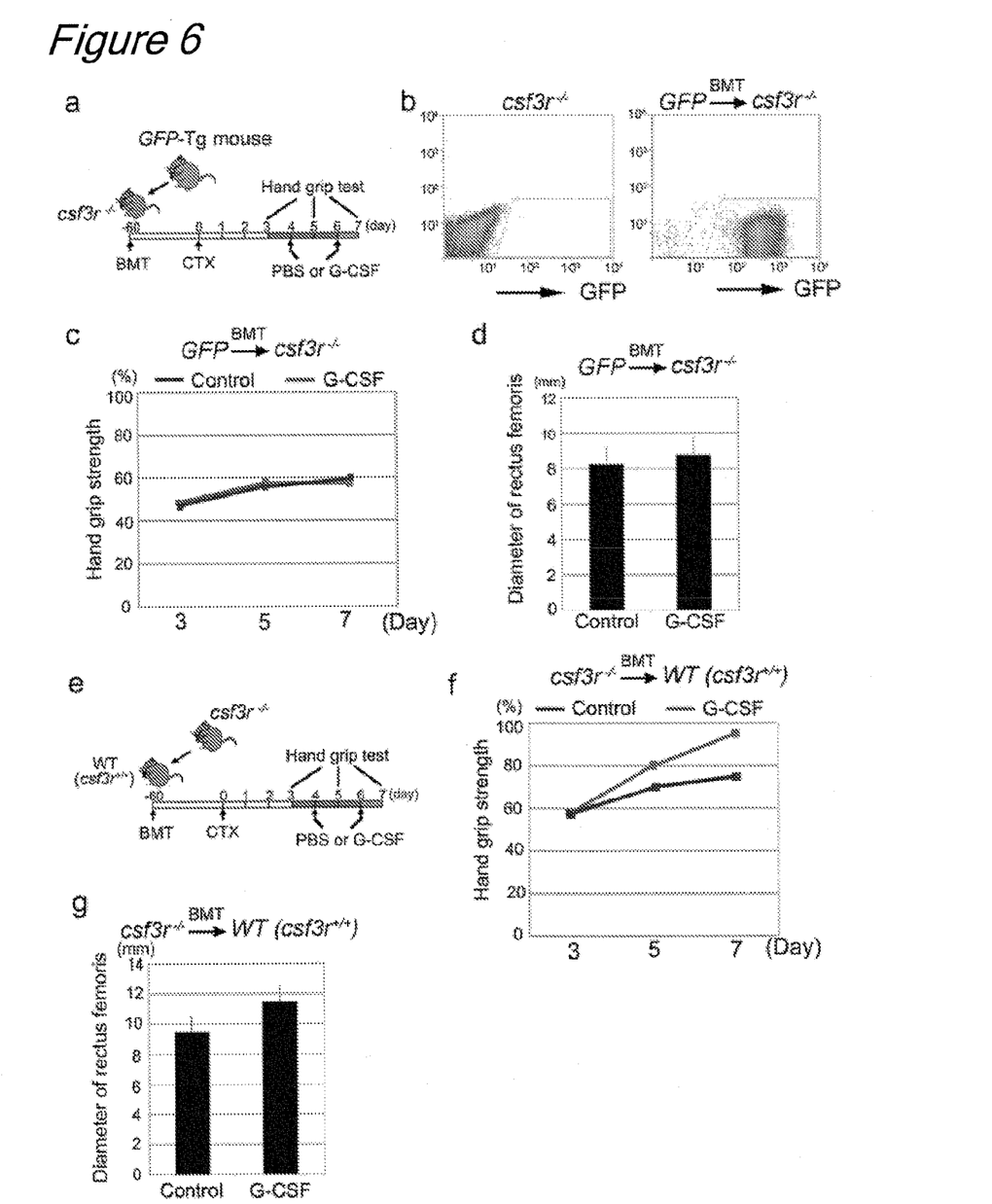

To prove the involvement of hematopoietic cells in the impairment of skeletal muscle regeneration in G-CSFR knockout mice, the bone marrow from csf3r$^{+/+}$ mice which constitutively express green fluorescent protein (GFP) was transplanted to csf3r$^{-/-}$ mice (FIG. 6a) 60 days prior to cardiotoxin injury. In all mice, it was ascertained by fluorescence activated cell sorting (FACS) analysis that bone marrow cells engrafted stably enough to give a chimerism in excess of at least 80% (FIG. 6b). Cardiotoxin was injected into the rectus femoris and G-CSF was administered (100 μl each at a concentration of 50 μg/ml) at days 4 and 6. After the cardiotoxin injection, the csf3r$^{-/-}$ mice transplanted with the bone marrow of csf3r$^{+/+}$ mice did not have any sign of improvement in a handgrip strength test even when they were administered G-CSF (FIG. 6c). The diameter of the rectus femoris was also not improved by G-CSF (FIG. 6d).

Next, the present inventors performed a bone marrow transplantation experiment in a reversed way: the bone marrow of the csf3r$^{-/-}$ mice was transplanted into the csf3r$^{+/+}$ mice. After skeletal muscle injury was caused in these mice, the regeneration of skeletal myocytes was induced by G-CSF (FIG. 6e). A handgrip strength test revealed that G-CSF markedly improved the strength of handgrip (FIG. 6f) and the diameter of rectus femoris was also found to increase (as measured at day 7) (FIG. 6g).

The experiments described above confirmed that hematopoietic cells expressing the G-CSF receptor are not capable of recovering the skeletal muscle regenerating ability of G-CSF receptor knockout mouse. Hence, the foregoing results have revealed that the action of G-CSF in the process of skeletal muscle regeneration is a direct effect on skeletal muscle and is not mediated by bone marrow cells.

The invention claimed is:

1. A method for promoting skeletal muscle repair, or treating skeletal muscle injury, comprising
administering an effective amount of granulocyte colony stimulating factor (G-CSF) locally within a period of 2-10 days after muscle injury, wherein the G-CSF is administered directly at a site of skeletal muscle injury by subcutaneous, intradermal or intramuscular administration.

2. The method according to claim 1, wherein the local administration is intramuscular administration.

3. The method according to claim 1, wherein the granulocyte colony stimulating factor is administered at an interval of 4 days.

4. The method according to claim 1, wherein the granulocyte colony stimulating factor is administered in a dosage of 0.1-10 μg/kg per single administration.

5. The method according to claim 4, wherein the granulocyte colony stimulating factor is administered in a dosage of 0.5-5 μg/kg per single administration.

6. The method according to claim 5, wherein the granulocyte colony stimulating factor is administered in a dosage of 1-2.5 μg/kg per single administration.

7. The method according to claim 4, wherein the granulocyte colony stimulating factor is administered in a total dosage of 0.2-50 μg/kg.

8. The method according to claim 7, wherein the granulocyte colony stimulating factor is administered in a total dosage of 1.0-25 μg/kg.

9. The method according to claim 8, wherein the granulocyte colony stimulating factor is administered in a total dosage of 2.0-12.5 μg/kg.

10. The method according to claim 5, wherein the granulocyte colony stimulating factor is administered in a total dosage of 0.2-50 μg/kg.

11. The method according to claim 10, wherein the granulocyte colony stimulating factor is administered in a total dosage of 1.0-25 μg/kg.

12. The method according to claim 11, wherein the granulocyte colony stimulating factor is administered in a total dosage of 2.0-12.5 μg/kg.

13. The method according to claim 6, wherein the granulocyte colony stimulating factor is administered in a total dosage of 0.2-50 μg/kg.

14. The method according to claim 13, wherein the granulocyte colony stimulating factor is administered in a total dosage of 1.0-25 μg/kg.

15. The method according to claim 14, wherein the granulocyte colony stimulating factor is administered in a total dosage of 2.0-12.5 μg/kg.

* * * * *